(12) United States Patent
Tully

(10) Patent No.: US 10,274,401 B2
(45) Date of Patent: Apr. 30, 2019

(54) EXHAUST FLOW TUBE SYSTEM FOR USE WITH EMISSIONS TEST EQUIPMENT AND ASSOCIATED PARTS AND SYSTEMS

(71) Applicant: Horiba Mira Limited, Nuneaton (GB)

(72) Inventor: Kevin Tully, Nuneaton (GB)

(73) Assignee: Horiba Mira Limited (GB)

( * ) Notice: Subject to any disclaimer, the term of this patent is extended or adjusted under 35 U.S.C. 154(b) by 92 days.

(21) Appl. No.: 15/348,445

(22) Filed: Nov. 10, 2016

(65) Prior Publication Data

US 2017/0131180 A1    May 11, 2017

(30) Foreign Application Priority Data

Nov. 11, 2015    (GB) .................................. 1519926.8
Feb. 8, 2016    (GB) .................................. 1602258.4

(51) Int. Cl.
*G01M 15/10*    (2006.01)
*F01N 13/08*    (2010.01)
(Continued)

(52) U.S. Cl.
CPC ............. *G01M 15/102* (2013.01); *F01N 9/00* (2013.01); *F01N 11/00* (2013.01); *F01N 13/08* (2013.01);
(Continued)

(58) Field of Classification Search
CPC .. G01M 15/102; Y02T 10/47; F01N 2560/07; F01N 13/08; G01N 1/2252
See application file for complete search history.

(56) References Cited

U.S. PATENT DOCUMENTS 3,917,454 A * 11/1975 Clark .................. G01M 15/102
422/83
4,727,746 A * 3/1988 Mikasa ............... G01M 15/102
73/114.71
(Continued)

FOREIGN PATENT DOCUMENTS

FR        2702839 A1    9/1994
JP       62298721 A   12/1987
(Continued)

OTHER PUBLICATIONS

Combined Search and Examination Report for GB application GB1602258.4, dated Apr. 4, 2016, pp. 1 to 7.
(Continued)

*Primary Examiner* — Freddie Kirkland, III
(74) *Attorney, Agent, or Firm* — Waller Lansden Dortch & Davis, LLP; Matthew C. Cox

(57) ABSTRACT

Provided is an exhaust flow tube system for use with emissions test equipment, the system comprising: a primary flow tube configured to receive exhaust gases from an engine exhaust pipe and to deliver the exhaust gases to emissions test equipment; a secondary flow tube configured to receive exhaust gases from the engine exhaust pipe and to deliver the exhaust gases to the emissions test equipment; a valve configured to control the flow of exhaust gases through the secondary flow tube; and a control system configured to receive a signal indicative of the flow rate or likely flow rate of exhaust gases from the engine exhaust, and to control the operation of the valve to alter the flow of exhaust gases through the secondary flow tube dependent on the signal.

19 Claims, 6 Drawing Sheets

(51) Int. Cl.
*F01N 9/00* (2006.01)
*F01N 11/00* (2006.01)
*G01N 21/3504* (2014.01)
*G01N 21/76* (2006.01)

(52) U.S. Cl.
CPC ...... *F01N 2240/36* (2013.01); *F01N 2390/00* (2013.01); *F01N 2410/00* (2013.01); *F01N 2560/07* (2013.01); *F01N 2900/0416* (2013.01); *F01N 2900/1411* (2013.01); *G01N 21/3504* (2013.01); *G01N 21/76* (2013.01); *Y02T 10/47* (2013.01)

(56) References Cited

U.S. PATENT DOCUMENTS

| | | | |
|---|---|---|---|
| 5,279,146 A | 1/1994 | Asano et al. | |
| 5,907,109 A * | 5/1999 | Tedeschi | G01N 1/26 73/864.73 |
| 6,443,021 B2 * | 9/2002 | Hanashiro | G01N 1/2258 73/863.11 |
| 6,739,184 B2 * | 5/2004 | Brazeau | G01M 15/10 73/114.69 |
| 6,789,413 B2 * | 9/2004 | Brazeau | G01M 15/10 73/114.71 |
| 6,813,882 B2 | 11/2004 | Hepburn et al. | |
| 7,389,703 B2 * | 6/2008 | Wei | G01M 15/102 73/863.03 |
| 7,454,950 B2 * | 11/2008 | Nakamura | G01N 33/0032 73/23.31 |
| 7,946,160 B2 * | 5/2011 | LaPree | G01M 15/102 73/114.71 |
| 8,429,957 B2 * | 4/2013 | Stedman | G01M 15/108 73/114.71 |
| 8,505,276 B2 * | 8/2013 | Nakamura | F01N 11/00 60/276 |
| 8,996,231 B2 * | 3/2015 | Uratani | G01M 17/00 701/29.1 |
| 9,151,202 B2 * | 10/2015 | Norris | F01N 3/2066 |
| 9,476,797 B2 * | 10/2016 | Uratani | G01M 15/102 |
| 9,593,618 B2 * | 3/2017 | Runde | F01N 13/008 |
| 2002/0178716 A1 | 12/2002 | Hepburn et al. | |
| 2003/0192369 A1 * | 10/2003 | Brazeau | G01M 15/10 73/116.02 |
| 2006/0236752 A1 | 10/2006 | Nakamura | |
| 2007/0068236 A1 * | 3/2007 | Wei | G01M 15/102 73/114.76 |
| 2012/0204542 A1 * | 8/2012 | Norris | F01N 3/2066 60/274 |
| 2015/0369108 A1 * | 12/2015 | Norris | F01N 3/2066 60/274 |
| 2016/0115850 A1 * | 4/2016 | Otsuki | F01N 11/002 417/472 |

FOREIGN PATENT DOCUMENTS

WO 2007010664 A1 1/2007
WO 2012051273 A1 4/2012

OTHER PUBLICATIONS

Examination Report for GB application GB1602258.4, dated Aug. 1, 2016, pp. 1 to 3.

* cited by examiner

EXHAUST FLOW TUBE SYSTEM FOR USE WITH EMISSIONS TEST EQUIPMENT AND ASSOCIATED PARTS AND SYSTEMS

CROSS-REFERENCE TO RELATED APPLICATIONS

This patent claims priority under 35 U.S.C. Section 119 to UK Patent Application No. 1519926.8 filed on 11 Nov. 2015 in the United Kingdom and to UK Patent Application No 1602258.4 filed on 8 Feb. 2016 in the United Kingdom. The entire content of each of these earlier-filed applications is hereby incorporated by reference for all purposes.

BACKGROUND

1. Field

The present disclosure relates generally to an exhaust flow tube system for use with emissions test equipment and associated parts and systems.

2. Description of the Related Art

The exhaust gas emissions of internal combustion engines used in vehicles are a major source air pollution and have come under close scrutiny in recent years. There are various standards and requirements for the exhaust gas emissions for new and existing vehicles (and also for internal combustion engines for other uses, such as generators). The accurate testing of exhaust emissions is important; however, the accurate testing of exhaust gas emissions is a difficult process.

SUMMARY

The following is a non-exhaustive listing of some aspects of the present techniques. These and other aspects are described in the following disclosure.

Embodiments of the present invention relate to an exhaust flow tube system for use with emissions test equipment, a network of tubes or conduits, a control system, an emissions measurement system, and a test facility. In particular, some embodiments of the present invention relate to equipment and systems for use in measurement of the exhaust gases from the operation of an internal combustion engine.

The exhaust gas emissions of internal combustion engines used in vehicles are a major source air pollution and have come under close scrutiny in recent years. There are various standards and requirements for the exhaust gas emissions for new and existing vehicles (and also for internal combustion engines for other uses, such as generators). The accurate testing of exhaust emissions is important; however, the accurate testing of exhaust gas emissions is a difficult process.

Standard tests have been devised during which a vehicle is driving through a test sequence on a rolling road. An exhaust pipe of the vehicle engine is connected, via a conduit, to test equipment which measures one or more aspects of the exhaust gas emissions—e.g. the amount of a particular gas present in a sample and the flow rate of exhaust gases.

However, such standard tests are not necessarily representative of the exhaust emissions during normal use of the vehicle. There is, therefore, a need to provide exhaust gas emissions testing equipment which can be used during normal operation of the vehicle (i.e. not operating according to a test sequence on a rolling road). This test equipment is, therefore, required to be portable and provided on or in the vehicle being tested.

Irrespective of whether the vehicle engine is being tested on a rolling road or whilst travelling on an actual road, it is necessary to measure the exhaust gases emitted from the vehicle engine exhaust pipe. This is typically achieved using a conduit connected to the vehicle engine exhaust pipe—the conduit directing exhaust gases to test equipment.

The flow rate of the exhaust gases emitted by a vehicle engine can vary considerably according to the operation of the vehicle engine. For example, when the engine is driven at a high speed (i.e. a high number of revolutions per minute) then the flow rate of exhaust gases is typically higher than when the engine is driven at a low speed.

The conduit which is connected to the exhaust pipe of the vehicle engine, to collect the exhaust gas emissions, are sized according to the expected flow rate of the exhaust gas emissions during the test. A conduit with too large a cross-section and accurate results cannot be obtained from low flow rates; however, too small a cross-section for the conduit and the test equipment effectively saturates and the results are not representative of the actual exhaust emissions.

FIG. 1 is a graph which shows the percentage error associated with gas flow rate measurements over a range of gas flow rates for three different sized conduits (Type B has an internal diameter of about 40 mm, Type C has an internal diameter of about 57 mm, and Type D has an internal diameter of about 72 mm). As can be seen, in general, the larger conduit diameter, the greater the error for low gas flow rates when measuring the gas flow rate through the conduit.

Whilst conventional tests using rolling roads and predetermined test sequences sometimes allow the selection of a conduit sized for reasonable accuracy of the test, developments in the testing and also in the vehicles mean that selecting a suitably sized conduit is no longer a straightforward task.

In particular, as test sequences encompass wider operating states of the vehicle (i.e. a wider range of engine speeds) then the sizing of the conduit to allow accurate results across all of these operating states is difficult. This is equally true of vehicle testing during normal operation of the vehicle. In addition, modern vehicles are using increasingly complicated mechanisms to minimise exhaust gas emissions, particularly at low engine speeds. For example, some vehicle engines may cease to operate all cylinders of the engine at idle or very low engine speeds. This can lead to very significant differences between exhaust gas emission flow rates during operation of the vehicle.

There is a need, therefore, to improve the accuracy of exhaust gas emissions testing equipment over a wide range of engine operating conditions.

This is emphasised by increasing pressure from governmental organisations to provide accurate and reliable testing equipment for exhaust gas emissions.

Accordingly, an aspect of the present invention provides an exhaust flow tube system for use with emissions test equipment, the system comprising: a primary flow tube configured to receive exhaust gases from an engine exhaust pipe and to deliver the exhaust gases to emissions test equipment; a secondary flow tube configured to receive exhaust gases from the engine exhaust pipe and to deliver the exhaust gases to the emissions test equipment; a valve configured to control the flow of exhaust gases through the secondary flow tube; and a control system configured to receive a signal indicative of the flow rate or likely flow rate of exhaust gases from the engine exhaust, and to control the operation of the valve to alter the flow of exhaust gases through the secondary flow tube dependent on the signal.

Another aspect provides an exhaust flow tube system for use with emissions test equipment, the system comprising: a primary flow tube configured to receive exhaust gases from an open end of an engine exhaust pipe and to deliver the exhaust gases to emissions test equipment; a secondary flow tube configured to receive exhaust gases from the open end of the engine exhaust pipe and to deliver the exhaust gases to the emissions test equipment; a valve configured to control the flow of exhaust gases through the secondary flow tube; and a control system configured to receive a signal indicative of the flow rate or likely flow rate of exhaust gases from the engine exhaust, and to control the operation of the valve to alter the flow of exhaust gases through the secondary flow tube dependent on the signal, wherein the open end of the engine exhaust pipe is the end through which exhaust gases are emitted to the atmosphere.

The signal indicative of the flow rate or likely flow rate may include a signal indicative of the rate of flow of gases through the primary flow tube.

The signal indicative of the flow rate or likely flow rate may include a signal indicative a control signal for operation of the engine.

The valve may be a butterfly valve.

The control system may be configured to receive the signal indicative of the flow rate or likely flow rate from the emission test equipment.

The first flow tube may have a different cross-sectional area to the second flow tube.

The valve may be actuatable between a first, closed, configuration and a second, open, configuration.

The valve may be actuatable to adopt a configuration between the first and second configurations.

The exhaust flow tube system may further include one or more further flow tubes configured to receive exhaust gases from the engine exhaust pipe and to deliver the exhaust gases to the emissions test equipment.

The exhaust flow tube system may further comprise a further valve configured to control the flow of exhaust gases through a one of the one or more further flow tubes.

The further flow tube may have a different cross-sectional area to at least one of the first and second flow tube.

Another aspect provides a network of tubes or conduits including a primary and a secondary flow tube for use in a system as above.

The network of tubes or conduits may further include the valve.

The network of tubes or conduits may further include the control system.

Another aspect provides a control system for use in a system as above or a network of tubes or conduits as above.

The control system may be configured to open the valve when the signal indicative of the flow rate or likely flow rate of exhaust gases from the engine exhaust exceeds a first predefined threshold.

The control system may be configured to close the valve when the signal indicative of the flow rate or likely flow rate of exhaust gases from the engine exhaust falls below a second predefined threshold.

The signal indicative of the flow rate or likely flow rate of exhaust gases from the engine exhaust may include a signal indicative of the rate of flow of gases through the primary flow tube.

The signal indicative of the flow rate or likely flow rate of exhaust gases from the engine exhaust may include a signal indicative a control signal for operation of the engine.

Another aspect provides an emissions measurement system including a system or network as above.

The emissions measurement system may be a portable emissions measurement system.

The emissions measurement system may be configured to be carried by a vehicle.

Another aspect provides a test facility including a system as above.

Another aspect provides a network of tubes or conduits for use in an exhaust flow tube system for use with emissions test equipment, the network including: a primary flow tube to receive exhaust gases from an engine exhaust pipe and to deliver the exhaust gases to emissions test equipment; a secondary flow tube to receive exhaust gases from the engine exhaust pipe and to deliver the exhaust gases to the emissions test equipment; and a valve to control the flow of exhaust gases through the secondary flow tube.

The network of tubes or conduits may further include a control system to receive a signal indicative of the flow rate or likely flow rate of exhaust gases from the engine exhaust pipe, and to control the operation of the valve to alter the flow of exhaust gases through the secondary flow tube dependent on the signal.

Another aspect provides a control system including a tangible computer readable medium which has instructions stored thereon which, when executed by a processor, cause the processor to: receive a signal indicative of the flow rate or likely flow rate of exhaust gases from an engine exhaust pipe into a primary flow tube and a secondary flow tube, the primary flow tube and the secondary flow tube being configured to deliver the exhaust gases to emissions test equipment; and control the operation of a valve to alter the flow of exhaust gases through the secondary flow tube dependent on the signal.

The tangible computer readable medium may have instructions stored thereon which, when executed by a processor, cause the processor to: open the valve when the signal indicative of the flow rate or likely flow rate of exhaust gases from the engine exhaust exceeds a first predefined threshold.

The tangible computer readable medium may have instructions stored thereon which, when executed by a processor, cause the processor to: close the valve when the signal indicative of the flow rate or likely flow rate of exhaust gases from the engine exhaust falls below a second predefined threshold.

The signal indicative of the flow rate or likely flow rate of exhaust gases from the engine exhaust may include a signal indicative of the rate of flow of gases through the primary flow tube.

The signal indicative of the flow rate or likely flow rate of exhaust gases from the engine exhaust may include a signal indicative a control signal for operation of the engine.

BRIEF DESCRIPTION OF THE DRAWINGS

Embodiments of the present invention are described, by way of example only, with reference to the accompanying drawings, in which.

Figure 1:
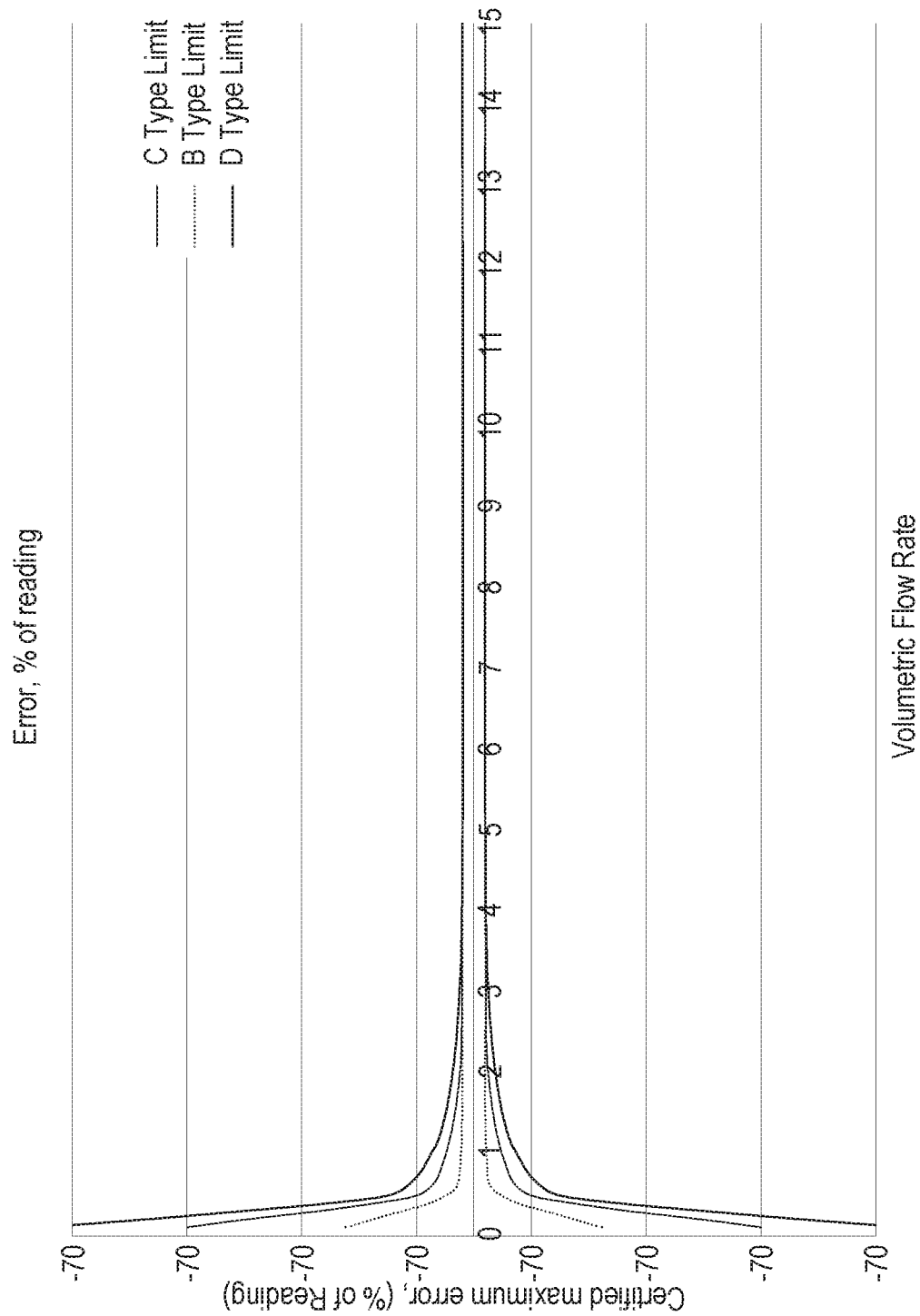
FIG. 1 shows a graph representing the flow rate errors for three given sizes of conduit (prior art)

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF CERTAIN EMBODIMENTS

Embodiments of the present invention include an exhaust flow tube system 1 which may include one or more conduits or tubes 2 connected together in a network.

The exhaust flow tube system 1 is configured to deliver exhaust gases from an engine exhaust pipe 3 to test emissions test equipment 4, through at least part of the one or more conduits or tubes 2.

The engine exhaust pipe 3 comprises an exhaust pipe from an internal combustion engine 5. The internal combustion engine 5 may be a petrol (i.e. gasoline) engine or a diesel engine, for example, and/or may be configured to burn one or more other forms of fuel.

Figure 2:
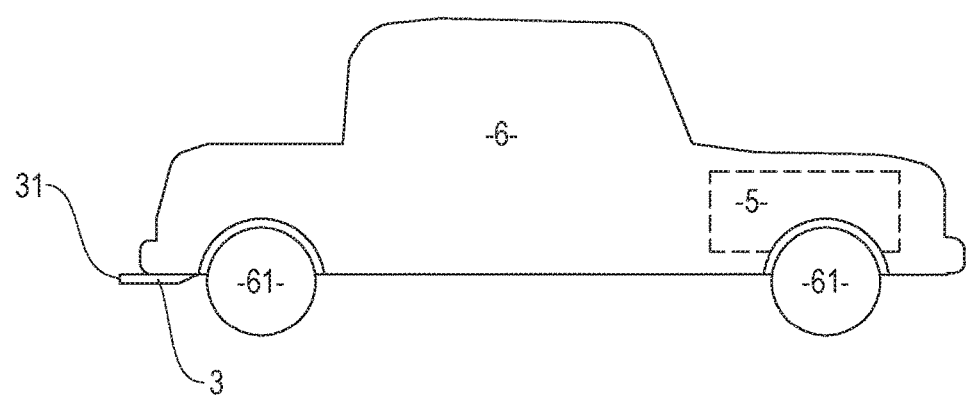
FIG. 2 shows a vehicle as used in some embodiments.

The internal combustion engine 5 may be mounted in a vehicle 6—see FIG. 2. The vehicle 6 may be a car, a truck, a lorry, a van, a bus, a coach, a motorcycle, or the like. Accordingly, the vehicle 6 may include a plurality of ground engaging wheels 61 which are coupled to the internal combustion engine 5, such that the internal combustion engine 5 is configured to drive rotation of at least one of the ground engaging wheels 61 (and hence movement of the vehicle 6 across the ground surface). In some embodiments, the vehicle 6 may include a track, the rotation of which is driven by internal combustion engine 5 to drive the vehicle 6 across the ground surface.

In some embodiments, the internal combustion engine 5 is a static engine—such as a generator.

The internal combustion engine 5 is configured to emit exhaust gases as a result of its operation (i.e. the gases resulting from combustion of a fuel within the internal combustion engine 5). The engine exhaust pipe 3 is configured to deliver these exhaust gases to the atmosphere.

In some embodiments, the internal combustion engine 5 includes a plurality of such engine exhaust pipes 3 and, in some embodiments, one engine exhaust pipe 3 is fed by a plurality of exhaust pipes via a manifold.

The or each engine exhaust pipe 3 includes an open end 31 through which the exhaust gases are emitted to the atmosphere (i.e. a tailpipe).

Figure 3:
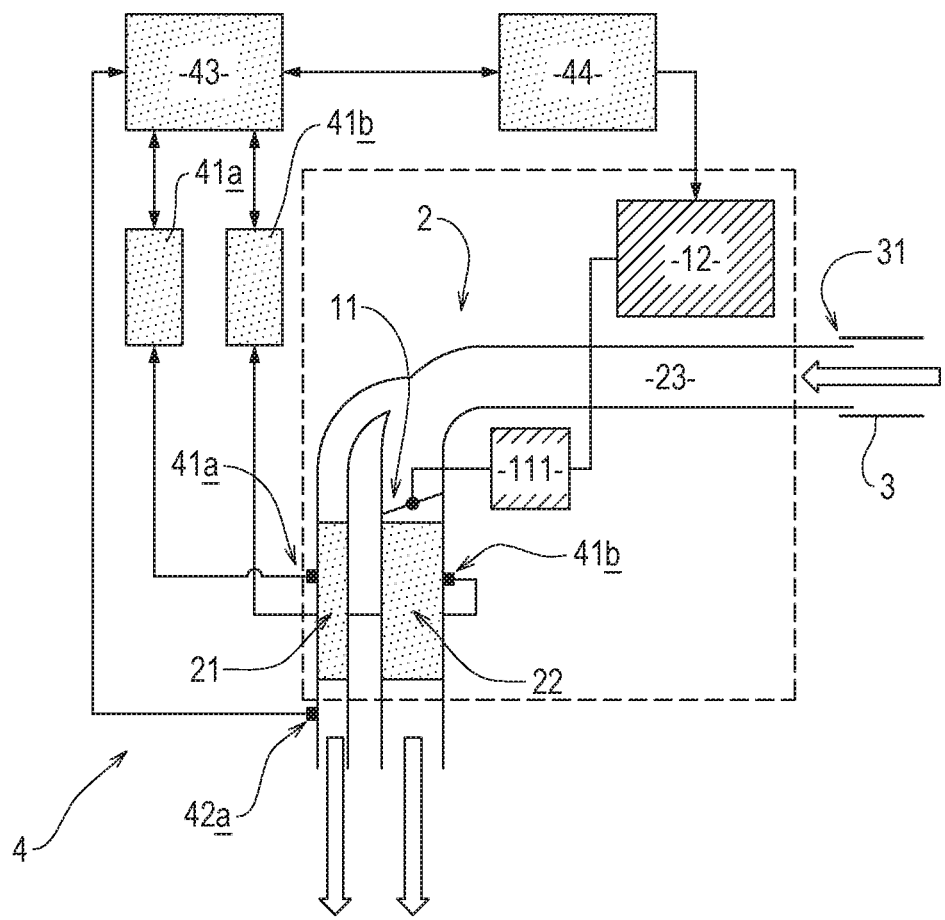
FIG. 3 shows an exhaust flow tube system and emission test equipment of some embodiments.

The exhaust flow tube system 1 (see FIG. 3) is configured to be fitted to the open end 31 of the or each engine exhaust pipe 3. Accordingly, at least some of the one or more tubes or conduits 2 are configured to receive exhaust gases from the or each engine exhaust pipe 3.

The flow tube system 1 may include one or more seals which ensure that substantially all of the exhaust gases from the open end 31 of the or each engine exhaust pipe 3 pass to the fitted exhaust flow tube system 1.

The one or more tubes or conduits 2 include a primary flow tube 21 and a secondary flow tube 22. Both the primary and secondary flow tubes 21,22 are configured to receive exhaust gases from at least one of the one or more engine exhaust pipes 3 to which the exhaust flow tube system 1 has been fitted. The primary and secondary flow tubes 21,22 are connected in parallel with each other such that exhaust gases may pass through either the first or the secondary flow tube 21,22 but the same exhaust gases do not flow through both the primary and secondary flow tubes 21,22 consecutively.

The exhaust flow tube system 1 may include a delivery tube 23. The delivery tube 23 is configured to be coupled to the open end 31 of the engine exhaust pipe 3 in fluid communication therewith. The delivery tube 23 may be further coupled in fluid communication with the primary flow tube 21 and the secondary flow tube 22 such that exhaust gases may pass through the delivery tube 23 to the primary and secondary flow tubes 21,22.

In some embodiments, the delivery tube 23 and the secondary flow tube 22 are of substantially the same internal cross-sectional area (e.g. substantially the same diameter). The primary flow tube 21 may be, in embodiments, of a smaller cross-sectional area (e.g. a smaller diameter) than one or both of the delivery tube 23 and the secondary flow tube 22.

The secondary flow tube 21 may be angled with respect to the delivery tube 23. In some embodiments, this angled arrangement may be achieved by bending a tube to define the delivery tube 23 and the secondary flow tube 22. The primary flow tube 21 may be located such that it is configured to be in fluid communication with the delivery tube 23, e.g. at the junction between the delivery tube 23 and the secondary flow tube 22 (which may be at a bend, as mentioned above). In some embodiments in which the secondary flow tube 22 is angled with respect to the delivery tube 23, the primary flow tube 21 may be coupled in fluid communication with the delivery tube 23 at or towards an outer part of the angled junction between the delivery tube 23 and the secondary flow tube 22 (e.g. on a convex part of the junction).

In some embodiments, the primary flow tube 21 is secured to the secondary flow tube 22 and/or delivery tube 23 by welding. The primary flow tube 21, secondary flow tube, and/or delivery tube 23 may be formed at least in part from steel (e.g. stainless steel). In some embodiments, these tubes 21,22,23 and may be also one or more of any other tubes or conduits 2 of the exhaust flow tube system 1 may be so formed from steel (e.g. stainless steel) and may include one or more seals, cuffs, and/or collars which may be formed from a different material (e.g. a plastics or rubber material).

The exhaust flow tube system 1 includes a valve 11 configured to control the flow of gases through the secondary flow tube 22. Accordingly, the valve 11 may be associated with the secondary flow tube 22. The valve 11 may be located at an entrance of the secondary flow tube 22, or along a length thereof.

The valve 11 may take a number of different forms but, in some embodiments, may be in the form of a butterfly valve.

The valve 11 is operable to be actuated between a first configuration in which the flow of gas therethrough (and, hence, through the secondary flow tube 22) is substantially prevented and a second configuration in which the flow of as therethrough (and, hence, through the secondary flow tube 22) is substantially permitted. In some embodiments, the valve 11 is operable to adopt a plurality of configurations between the first and second configuration—to vary the flow of gas through the valve 11 (e.g. partially open valve configurations.

The valve 11 may, therefore, include a valve actuator 111 which is configured to drive the operation of the valve 11 (i.e. its actuation between the first and second configurations). The valve actuator 111 may include, for example, an electromechanical device—such as a motor, a servomotor, or a solenoid, for example.

The valve actuator 111 is configured to receive a command signal from a control system 12 of the exhaust flow tube system 1. The control system 12 may be coupled, therefore, to the valve actuator 111 via a wired or wireless communication channel over which the command signal may be transmitted.

The command signal may be a command for the valve 11 to be in the first configuration or the second configuration. The command signal may, in some embodiments, be a signal for the valve 11 to be in a configuration between the first and second configurations—as described herein. Accordingly, the valve actuator 111 may be configured to receive the command signal and to control the operation of the valve 11 to the desired configuration.

The valve actuator 111 may be configured, for example, to determine the current configuration of the valve 11, to compare this to the configuration indicated in the command signal, and to actuate the valve 11 based on this comparison. In some embodiments, the valve actuator 111 does not perform this function—which may be performed by the control system 12 instead.

The control system 12 is configured to receive a signal indicative of the flow rate or likely flow rate of exhaust gases from the engine exhaust pipe, and to control the operation of the valve 11 (e.g. using the valve actuator 111) to alter the flow of exhaust gases through the secondary flow tube dependent on the signal.

The control system 12 may, in some embodiments, be configured to receive a signal indicative of the engine speed (e.g. revolutions per minute of an output shaft of the internal combustion engine or another measure of engine speed) as the signal indicative of the flow rate or likely flow rate of exhaust gases from the engine exhaust pipe.

In some embodiments, the control system 12 may be configured to receive a signal indicative of a future engine speed rather than a current engine speed. As will be appreciated, this would be an indicator of likely rate of flow of exhaust gases.

In some embodiments, this future engine speed may be determined based on a planned test sequence of the operation of the internal combustion engine 5 during use of the exhaust flow tube system 1. In some embodiments, this future engine speed may be determined based an acceleration signal (which may be received by the control system 12). The acceleration signal may be a signal indicative of an acceleration command provided to the internal combustion engine 5 to control its operation—such as, for example, a signal generated as the result of operation of an accelerator operator control (e.g. a pedal, lever, or the like). Accordingly, in some embodiments, the control system 12 may be communicatively coupled to an engine control system for the internal combustion engine 5 (e.g. a control system for the vehicle 6).

The control system 12 may be configured to use the rate of change of the flow of gases or the likely flow of gases (e.g. the future flow of gases) in its operation—to determine when and how to operate the valve 11. For example, sudden acceleration may be indicated by a sudden increase in the flow rate of the exhaust gases or some other recognisable characteristic, or may be determined from the acceleration signal. A high rate of increase in the flow of exhaust gases may be indicative of a high flow rate currently or in the future (e.g. in the near future). Likewise, a high rate of decrease in the flow of exhaust gases may be indicative of a low flow rate currently or in the future (e.g. in the near future).

In some embodiments, the control system 12 is communicatively coupled to the emissions test equipment 4 and configured to receive therefrom the signal indicative of the flow rate or likely flow rate of exhaust gases from the engine exhaust pipe. In such embodiments, that signal may be based on one or more other signals received by the emissions test equipment 4 regarding the operation of the internal combustion engine 5 (e.g. the current engine speed or future engine speed, generally as described above in relation to the signals received directly by the control system 12 in some embodiments but received indirectly, via the emissions test equipment 4, in other embodiments) or may be a signal indicative of a measured flow rate for the gases using the equipment of the emissions test equipment 4 or a combination of such signals (such as an indication of the current measured flow rate of exhaust gases in combination with an indication of current or future engine speed).

In some embodiments, the control system 12 is configured to control the operation of the valve 11 (using the valve actuator 111) based on the current flow rate of exhaust gases in the one or more tubes or conduits 2—e.g. in one or both of the primary and secondary flow tubes 21,22 and/or the delivery tube 23. In some embodiments, the control system 12 is configured to output the command signal to actuate the valve 11 from the first configuration to the second configuration based on a measured gas flow rate through the delivery tube 23 and/or the primary flow tube 21. The control system 12 may be configured to output the command signal to actuate the valve 11 from the second configuration to the first configuration based on a measured gas flow rate through the delivery tube 23 or through the primary and secondary flow tubes 21,22.

In some embodiments, the operation of the control system 12 is based at least in part on a comparison of the current flow rate of gases through the one or more tubes or conduits 2 (as described above) compared to at least one predetermined threshold. Once the gas flow rate falls below or exceeds the or each predetermined threshold, then an appropriate command signal is output to control the operation of the valve 11. In some embodiments, the or each predetermined threshold is a respective flow rate (e.g. in m3/min)—i.e. an absolute threshold—and, in some embodiments, the or each threshold is a respective relative threshold which is relative with respect to the operating range of flow rates of the exhaust flow tube system 1. For example, the or each threshold may be a percentage of the maximum flow rate for the exhaust flow tube system 1. In some embodiments, a mixture of absolute and relative thresholds are used—such that one threshold is a relative threshold and another is an absolute threshold. In any event, whether relative or absolute, the or each threshold is a predetermined flow rate.

In some embodiments, the control system 12 may be configured to control the operation of the valve 11 based at least in part on the rate of increase or decrease in the flow of exhaust gases. As such, the control system 12 may compare a current flow rate with one or more predetermined thresholds and control the operation of the valve 11 accordingly—using a suitable command signal. This rate of increase or decrease may be determined from measured flow rates—as described herein—or using an indicator of a likely rate of increase or decrease—such as may be obtained from control signals which control the operation of the internal combustion engine 5.

The control system 12 may be configured to control the operation of the valve 11 in accordance with a control regime which uses a mixture of inputs which may include one or more of the flow rate of gases through the one or more conduits or tubes 2, a control signal for the internal combustion engine 5, and one or more environmental factors (such as the current temperature, air pressure, humidity, or the like). The control system 12 may, accordingly, be configured to receive information concerning one or more environmental factors from an appropriate source of such information (e.g. one or more sensors).

The exhaust flow tube system 1 is configured to be coupled in fluid communication with the emissions test equipment 4. In particular, both the primary and secondary flow tubes 21,22 may be configured to be so coupled.

As will be appreciated, the coupling of the exhaust flow tube system 1 to the or each engine exhaust pipe 3 will be upstream of the coupling to the emissions test equipment 4—in relation to the direction of the flow of gases during normal operation.

The emissions test equipment 4 may include one or more probes 41 which extend into the flow of gas through the primary and/or secondary flow tubes 21,22. In some embodiments, a first probe 41a is configured to sense a parameter associated with gases flowing through the primary flow tube 21 and a second probe 41b is configured to sense a parameter associated with gases flowing through the secondary flow tube 21. In some embodiments, the or each probe 41 may include a probe to measure the flow rate of gas through the primary and/or secondary flow tubes 21,22, as the case may be. In some embodiments, the probe to measure the flow rate of gas may include a Pitot tube with an associated transducer module. In some embodiments, the probe to measure the flow rate of gas may include an Ultrasonic Exhaust Flow Meter, such as the EXFM-ONE of the HORIBA Group, Japan.

In some embodiments, because of the use of a plurality of flow tubes (e.g. the primary and secondary flow tubes 21,22), the flow rate in each flow tube is reduced compared systems having only one flow tube. Accordingly, the use of Ultrasonic Exhaust Flow Meter, or other probe with limited flow rate ranges, may be more viable in accordance with some embodiments than was previously considered possible. Similarly, in some embodiments, the reduced flow rate in each flow tube reduces back pressure issues which may result from intrusions onto the confines of the flow tubes—e.g. the or each probe 41.

In some embodiments, the use of a plurality of flow tubes, the flow through one or more of which is controlled by one or more respective valves 11, can resolve or reduce backflow/backpressure issues when a high flow rate of gas is expected. In some such embodiments, the use of the plurality of flow tubes may not be needed for accuracy at low flow rates—as is the case in some embodiments described herein—but may still resolve or reduce backflow/pressure issues. These backflow/backpressure issues may impact measurements taken by embodiments (e.g. by the emissions test equipment 4) and/or may impact the operation of the internal combustion engine 5—for example, in an engine 5 with a low pressure exhaust gas recirculation system.

In some embodiments, the emissions test equipment 4 may include one or more sample tubes 42 which are each configured to extract a sample of gas from the gas flowing through the primary and/or secondary flow tubes 21,22 for analysis by another part of the emissions test equipment 4. In some embodiments, a first such sample tube 42a is associated with the primary flow tube 21 and a second such sample tube is associated with the secondary flow tube 22. The one or more sample tubes 42 may be in fluid communication with a inlet of the emissions test equipment 4 and that inlet may be a common inlet for all of the one or more sample tubes 42 (e.g. for both the first and second sample tubes 42a).

The emissions test equipment 4 may include one or more test modules 43, which may include one or more of a non-dispersive infrared detection system, a chemiluminescence detection system, and/or a flame ionization detection system. These one or more test modules 43 may be, for example, configured to receive gas via the one or more sample tubes 42 and the inlet of the emissions test equipment 4. The one or more test modules 43 (and, therefore, the emissions test equipment 4) may be configured to receive a wet gas sample. The one or more test modules 43 (and, therefore, the emissions test equipment 4) may be configured to determine the volume of one or more target gases in a gas sample and/or one or more particles carried in the gas sample. These target gases and/or particles may include, for example one or more pollutants or green house gases. The target gases may include carbon oxides (e.g. carbon monoxide), nitrogen oxides, and hydrocarbons.

In some embodiments, the emissions test equipment 4 may include a data recorder 44 which is configured to record data output by the or each test module 43. In some embodiments, the data recorder 44 is provided as a separate unit to the one or more test modules 43 and may be communicatively coupled thereto.

In some embodiments, the control system 12 is communicatively coupled to the data recorder 44 and the signals discussed herein as being sent by the emissions test equipment 4 to the control system 12 may be signals sent by the data recorder 44.

In some embodiments, the data recorder 44—or another part of the emissions test equipment 4—provides some or substantially all the above described functionality of the control system 12.

Embodiments may include a tangible computer readable medium which has stored thereon instructions to control the operation of a computer to provide the control regime described above. The computer may, for example, form part of the emissions test equipment 4 and/or control system 12. In some embodiments, the control system 12 is provided as a dedicated circuit which may include a microcontroller or a field programmable gate array, or the like.

As will be appreciated, an exhaust flow tube system 1 with a primary and a secondary flow tube 21,22 has been described. In some embodiments, a tertiary flow tube (not shown) may be provided and in some embodiments more than three flow tubes may be provided—with the flow tubes connected in parallel in an arrangement corresponding with that of the primary and secondary flow tubes 21,22 described herein.

In some embodiments with more than two flow tubes, one or more of the flow tubes may have a different cross-sectional area to one or more of the other flow tubes. In some embodiments, each flow tube may have a different cross-sectional area to all of the other flow tubes. In some embodiments, one or more of the flow tubes may have a valve corresponding with the valve 11 in the secondary flow tube 22 as described herein—to control the flow of gas therethrough. Each such valve may be associated with one or more valve actuators (corresponding with the valve actuator 111 described herein) which may be configured to be driven in unison and/or independently to actuate the valves between their respective first and second configurations. The valves (e.g. via the or each valve actuator) may be coupled to their own respective control system (corresponding with control system 12 described above) or to a common control system 12 which is configured to control the operation of the valves. If a plurality of control systems 12 is provided then the control systems may be configured to communicate with each other to provide the desired operation—as described herein.

In some embodiments, all of the flow tubes (e.g. both the primary and secondary flow tubes 21,22) are associated with respective valves 11 as described herein. Accordingly, valves 11 in each flow tube (including the primary and secondary flow tubes 21,22) may be configured to control the flow of gases therethrough. The valves 11 may be located at respective entrances of the associated flow tubes, or along a length thereof. Each valve 11 may be coupled to its own valve actuator 111 or there may be a common valve actuator 111. Similarly, each valve 11 may be coupled to its own control system 12 or a common control system 12.

In embodiments with more than two flow tubes, it will be appreciated that the associated valve or valves can be actuated between their respective first and second configurations in order to provide various different effective flow tube cross-sectional areas.

The effective flow tube cross-sectional area of a given exhaust flow tube system 1 of embodiments is determined by the cross-sectional areas of the flow tubes forming part of that exhaust flow tube system 1 and the configuration of the or each valve associated therewith. Accordingly, a single exhaust flow tube system 1 may provide a plurality of different effective flow tube cross-sectional areas and the effective flow tube cross-sectional area may be varied over time (e.g. dependent on the operation of the internal combustion engine 5).

Figure 4:
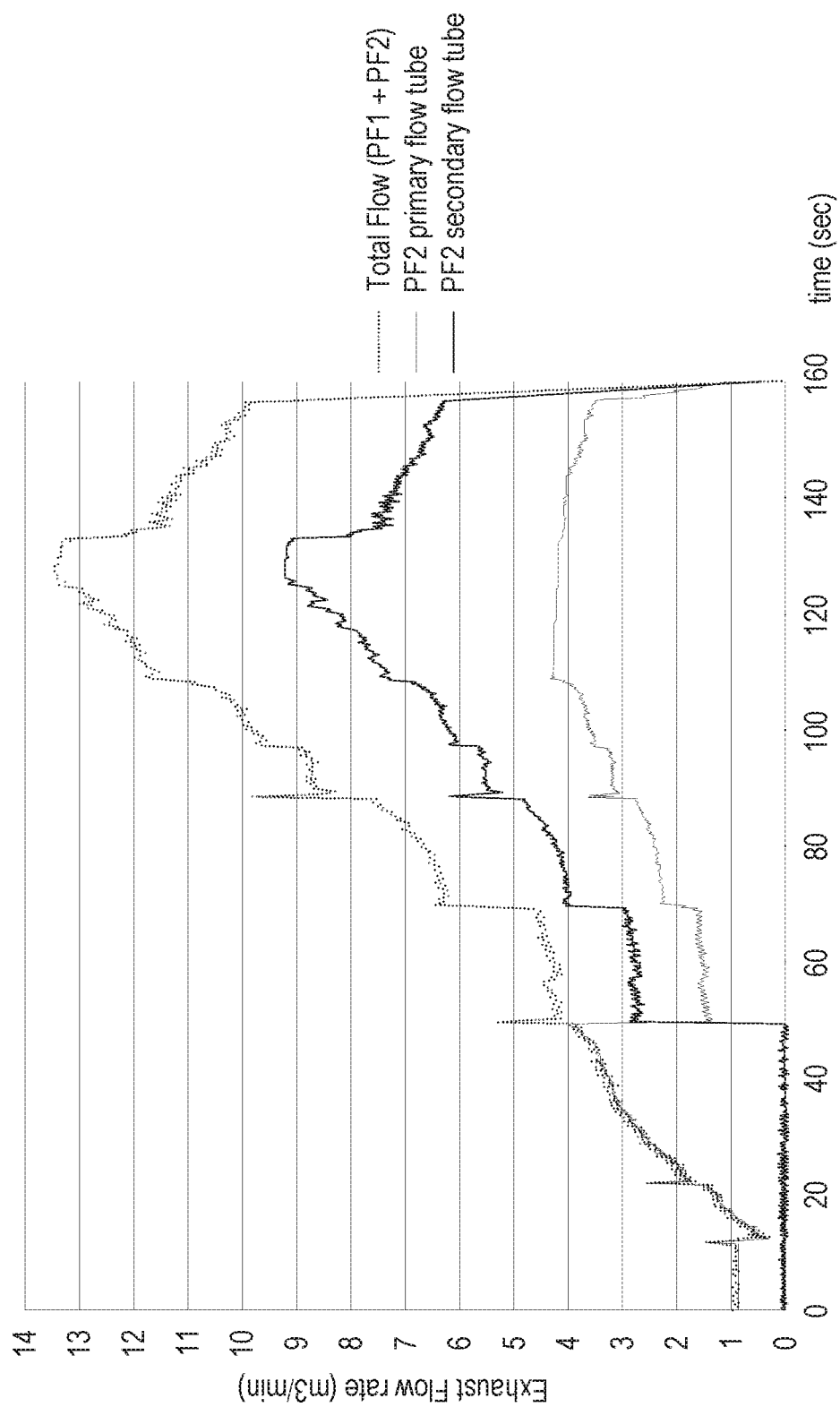
FIGS. 4 to 6 show graphs demonstrating the relationship between the total flow rate and the flow rates through the primary and secondary flow tubes.
Figure 5:
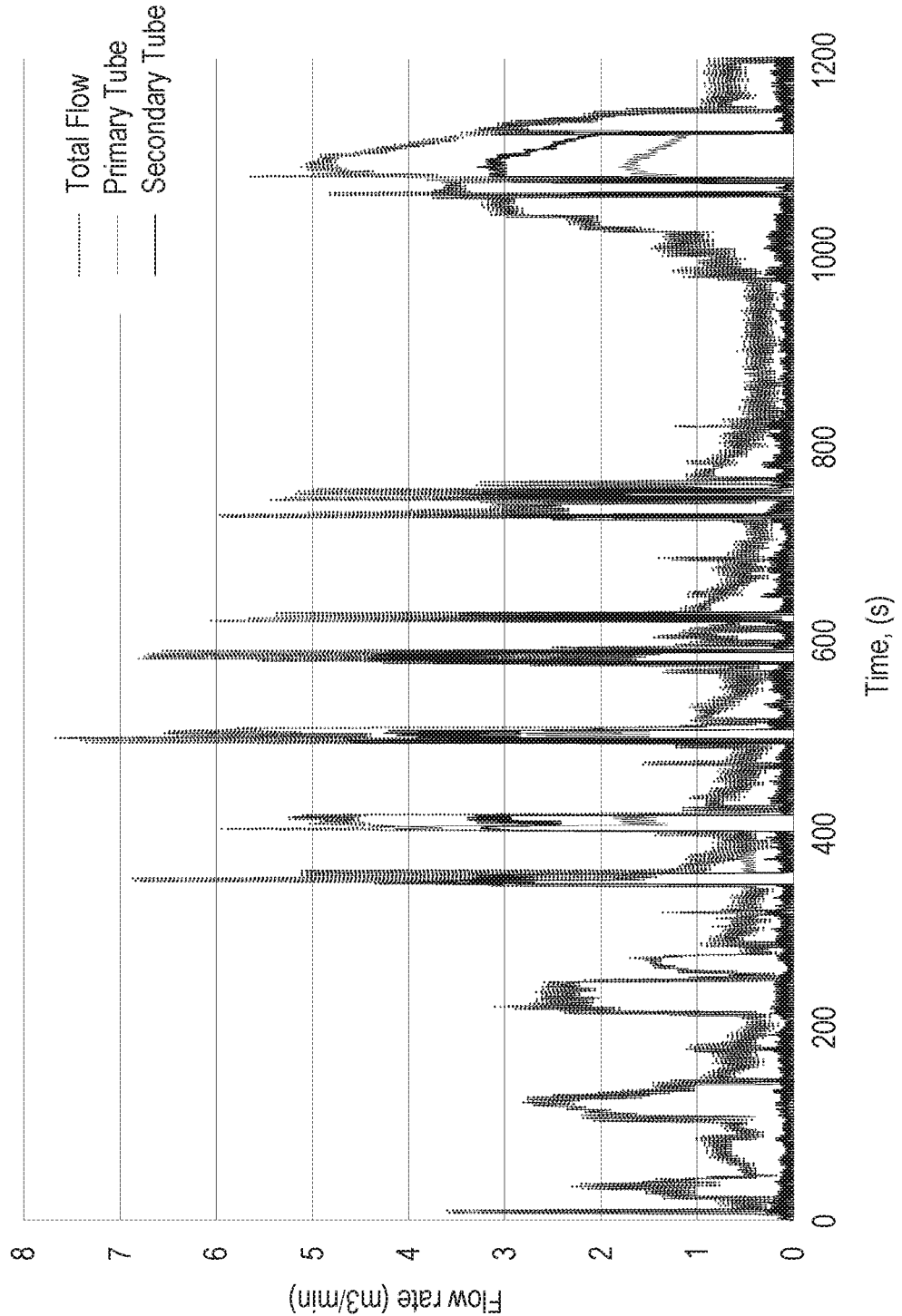
Figure 6:
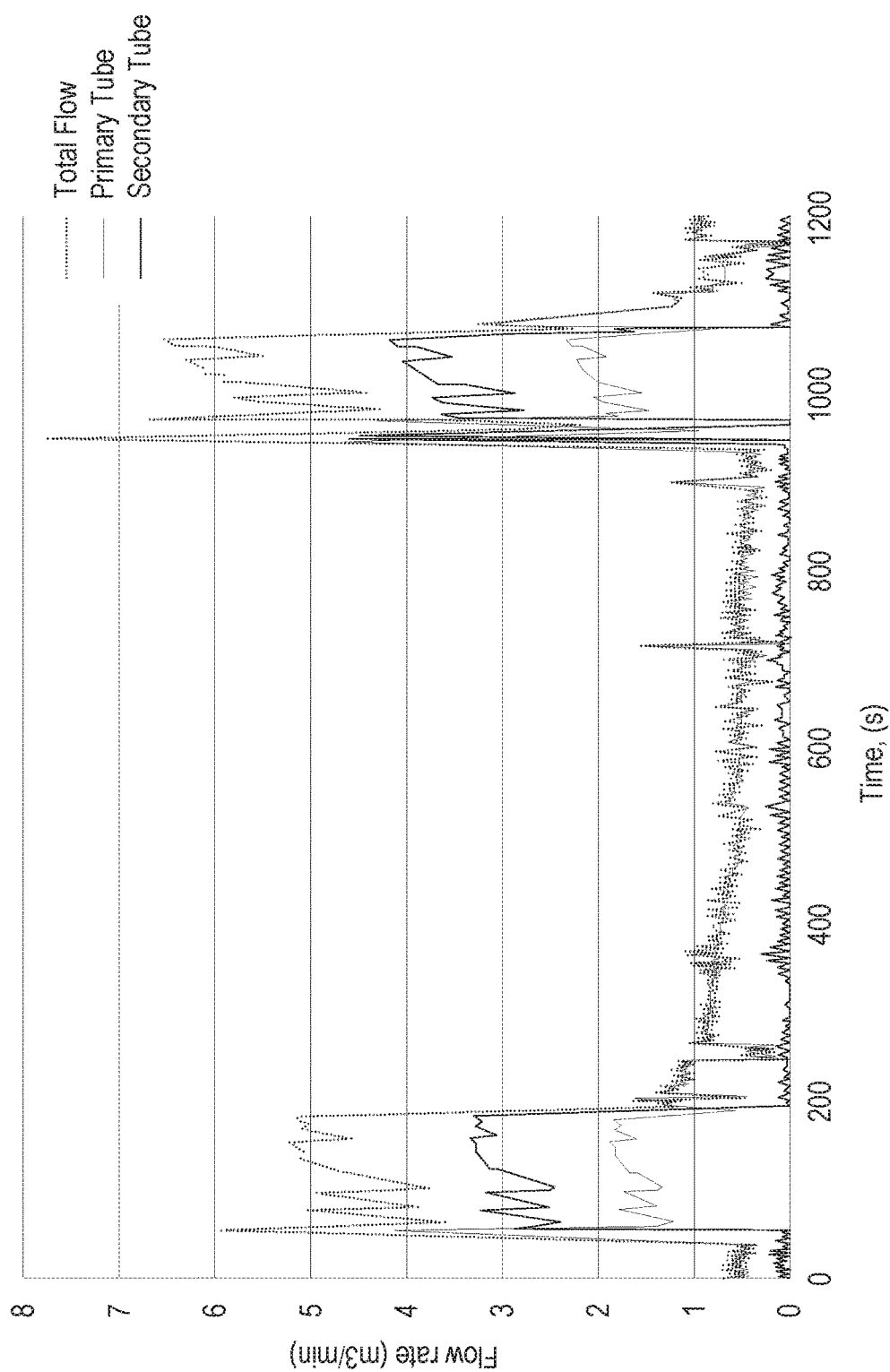

Accordingly, the total volume of gases through the exhaust flow tube system 1 will be the sum of the flow volume through each flow tube thereof (the flow tubes being provided in a parallel arrangement as described herein). FIGS. 4 to 6 show examples of the rate of gas flow through the primary flow tube 21, the secondary flow tube 22, and the total flow rate.

Each flow tube could have a circular cross-section in accordance with embodiments. The external diameters of the flow tubes may be, for example, 2.54 cm (1 inch), 3.81 cm (1.5 inches), 4.45 cm (1.75 inches), 5.08 cm (2 inches), 6.35 cm (2.5 inches), 7.62 cm (3 inches), 10.16 cm (4 inches), 12.7 cm (5 inches), or 15.24 cm (6 inches)— although other diameters are envisaged. For example, the external or internal diameters may be between 1 cm and 20 cm in some embodiments or between 2 cm and 16 cm in some embodiments.

As will be appreciated, embodiments of the present invention seek to provide a greater effective exhaust gas flow rate range of operation than prior systems. Accordingly, the control system 12 may operate to control the operation of the or each valve 11 to provide a relatively small effective cross-sectional area for the flow tubes when the flow rate of the exhaust gases is low, but will increase the effective cross-sectional area when the flow rate of the exhaust gases is high.

Some embodiments of the present invention also seek to provide a system which can be used in real-world testing of a vehicle 6 over a wide range of exhaust gas flow rates without the need for a conduit to be detached and replaced during the testing process—which is typically impractical in any event in conventional systems. Some embodiments of the present invention may be used with portable emissions measurement systems (e.g. the emissions test equipment 4 may be a portable emissions measurement system configured to be carried by the vehicle 6 of which the internal combustion engine 5 forms a part).

Some embodiments of the present invention may seek to be used instead of sets of interchangeable conduits which are prevalent in the prior art.

In some embodiments, the internal combustion engine 5 has a plurality of engine exhaust pipes 3 and a plurality of open ends 31. Accordingly, embodiments of the present invention may include exhaust flow tube systems 1 which are configured to be fitted to each of the plurality of open ends 31 of the engine exhaust pipes 3 at the same time— such that the total exhaust gas flow rate can be accurately determined. In some embodiments, each open end 31 may be associated with its own set of tubes or conduits 2 and a downstream manifold may be provided to combine the gases from all of the sets of tubes or conduits 2 into a single outlet pipe. The flow rate in each tube or conduit 2 may be determined and samples of the gas may be taken from each tube or conduit 2 or from the single outlet pipe, or both.

Embodiments of the invention may be particularly useful in seeking to obtain accurate indications of the volumes of exhaust gases emitted by an internal combustion engine 5 which is configured to have considerable variation in exhaust gas flow rates—e.g. a multi-cylinder engine in which only a subset of the cylinders operate when the engine 5 is idling but all of the cylinders operate when the engine 5 is under load. Such wide variations in flow rates for exhaust gases are becoming more common in relation to some internal combustion engines 5 as legislation places limits on or penalises high exhaust gas emission volumes. As will be appreciated, the emissions test equipment 4 of embodiments may be configured to determine gas emission volumes using the measured gas flow rates and may use other information it determines to provide an indication of the volumes of particular target gases.

As will be understood, gaining an accurate indication of the volumes of exhaust gases emitted by an internal combustion engine 5 is vital information to ensure that the engine 5 meets predefined targets—often designed to reduce pollution levels—and as part of the process of designing such engines 5 and their control systems (in order to keep vehicle emissions below predefined targets and to seek to reduce pollution levels).

Communicatively coupled parts of embodiments of the present invention may be coupled by wired or wireless communication channels. In some embodiments, coupled parts may communicate using digital or analogue signals— which may be using 0-5V, 0-3V, 0-12V or 0-16V signals for example.

References have been made herein to exhaust gas and gases. As will be appreciated, exhaust gas will typically comprise a plurality of component gases. The references should be construed accordingly.

Embodiments of the present invention may include a test facility which includes any of the systems disclosed herein. The test facility may include a test bay configured to receive an internal combustion engine 5 and/or a vehicle 6 including an internal combustion engine 5. The test bay may include a rolling road. The test bay may include equipment to define a test sequence for the operation of the internal combustion engine 5 and/or vehicle 6.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. An exhaust flow tube system and emissions test equipment combination, the exhaust flow tube system being for use with the emissions test equipment, the system configured to be fitted to an open end of an engine exhaust pipe, wherein the emissions testing equipment includes a probe and the exhaust flow tube system, the system comprising:
a primary flow tube configured to receive exhaust gases from the engine exhaust pipe and to deliver the exhaust gases to emissions test equipment;
a secondary flow tube configured to receive exhaust gases from the engine exhaust pipe and to deliver the exhaust gases to the emissions test equipment, wherein the open end of the engine exhaust pipe is the end through which exhaust gases are emitted to the atmosphere;
a valve configured to control a flow of exhaust gases through the secondary flow tube; and
a control system configured to receive a signal indicative of a flow rate or likely flow rate of exhaust gases from the engine exhaust, and to control the operation of the valve to alter the flow of exhaust gases through the secondary flow tube dependent on the signal, the control system being configured to operate to control the operation of the valve to provide relatively small effective cross-sectional area for the secondary flow tube when the flow rate of the exhaust gases is low and to increase the effective cross-sectional area when the flow rate of the exhaust gases is high, the probe extending into the flow of gas through the primary or secondary flow tube, such that the flow rate of the exhaust gases sensed by the probe is maintained within a limited flow rate range for the probe.

2. The exhaust flow tube system according to claim 1, wherein the signal indicative of the flow rate or likely flow rate includes a signal indicative of the rate of flow of gases through the primary flow tube.

3. The exhaust flow tube system according to claim 1, wherein the signal indicative of the flow rate or likely flow rate includes a signal indicative a control signal for operation of the engine.

4. The exhaust flow tube system according to claim 1, wherein the valve is a butterfly valve.

5. The exhaust flow tube system according to claim 1, wherein the control system is configured to receive the signal indicative of the flow rate or likely flow rate from the emission test equipment.

6. The exhaust flow tube system according to claim 1, wherein the first flow tube has a different cross-sectional area to the second flow tube.

7. The exhaust flow tube system according to claim 1, wherein the valve is actuatable between a first, closed, configuration and a second, open, configuration.

8. The exhaust flow tube system according to claim 7, wherein the valve is actuatable to adopt a configuration between the first and second configurations.

9. The exhaust flow tube system according to claim 1, further including one or more further flow tubes configured to receive exhaust gases from the engine exhaust pipe and to deliver the exhaust gases to the emissions test equipment.

10. The exhaust flow tube system according to claim 9, further comprising a further valve configured to control the flow of exhaust gases through a one of the one or more further flow tubes.

11. The exhaust flow tube system according to claim 9, wherein the further flow tube has a different cross-sectional area to at least one of the first and second flow tube.

12. A network of tubes or conduits for use in an exhaust flow tube system for use with emissions test equipment, the network including:
a primary flow tube to receive exhaust gases from an engine exhaust pipe and to deliver the exhaust gases to emissions test equipment;
a secondary flow tube to receive exhaust gases from the engine exhaust pipe and to deliver the exhaust gases to the emissions test equipment; and
a valve to control a flow of exhaust gases through the secondary flow by providing relatively small effective cross-sectional area for the secondary flow tube when a flow rate of the exhaust gases is low and to increase the effective cross-sectional area when the flow rate of the exhaust gases is high.

13. A network of tubes or conduits according to claim 12, further including a control system to receive a signal indicative of the flow rate or likely flow rate of exhaust gases from the engine exhaust pipe, and to control the operation of the valve to alter the flow of exhaust gases through the secondary flow tube dependent on the signal.

14. A control system including a tangible computer readable medium which has instructions stored thereon which, when executed by a processor, cause the processor to:
receive a signal indicative of a flow rate or likely flow rate of exhaust gases from an engine exhaust pipe into a primary flow tube and a secondary flow tube, the primary flow tube and the secondary flow tube being configured to deliver the exhaust gases to emissions test equipment; and
control the operation of a valve to alter a flow of exhaust gases through the secondary flow tube dependent on the signal including providing relatively small effective cross-sectional area for the secondary flow tube when the flow rate of the exhaust gases is low and to increase the effective cross-sectional area when the flow rate of the exhaust gases is high.

15. A control system according to claim 14, wherein the tangible computer readable medium has instructions stored thereon which, when executed by a processor, cause the processor to:
open the valve when the signal indicative of the flow rate or likely flow rate of exhaust gases from the engine exhaust exceeds a first predefined threshold.

16. A control system according to claim 15, wherein the tangible computer readable medium has instructions stored thereon which, when executed by a processor, cause the processor to:
close the valve when the signal indicative of the flow rate or likely flow rate of exhaust gases from the engine exhaust falls below a second predefined threshold.

17. A control system according to claim 15, wherein the signal indicative of the flow rate or likely flow rate of exhaust gases from the engine exhaust includes a signal indicative of the rate of flow of gases through the primary flow tube.

18. A control system according to claim 15, wherein the signal indicative of the flow rate or likely flow rate of exhaust gases from the engine exhaust includes a signal indicative a control signal for operation of the engine.

19. A vehicle including:

an exhaust flow tube system for use with emissions test equipment;

an internal combustion engine mounted in the vehicle; and an engine exhaust pipe configured to deliver exhaust gases from the engine to the atmosphere through an open end of the engine exhaust pipe, wherein the exhaust flow tube system is configured to be fitted to the open end of an engine exhaust pipe and comprises:

- a primary flow tube configured to receive exhaust gases from the open end of the engine exhaust pipe and to deliver the exhaust gases to emissions test equipment;
- a secondary flow tube configured to receive exhaust gases from an open end of the engine exhaust pipe and to deliver the exhaust gases to the emissions test equipment;
- a valve configured to control the flow of exhaust gases through the secondary flow tube; and
- a control system configured to receive a signal indicative of the flow rate or future flow rate of exhaust gases from the engine exhaust, and to control the operation of the valve to alter the flow of exhaust gases through the secondary flow tube dependent on the signal, the control system being configured to operate to control the operation of the valve to provide a relatively small effective cross-sectional area for the secondary flow tube when the flow rate of the exhaust gases is low and to increase the effective cross-sectional area when the flow rate of the exhaust gases is high.

* * * * *